United States Patent [19]

Shih et al.

[11] 4,026,767

[45] May 31, 1977

[54] TEST PROCEDURE FOR MICROORGANISMS IN BLOOD

[75] Inventors: Chun-Nan Shih, East Lansing, Mich.; Edward Balish, Madison, Wis.

[73] Assignee: Wisconsin Alumni Research Foundation, Madison, Wis.

[22] Filed: Nov. 19, 1975

[21] Appl. No.: 633,278

[52] U.S. Cl. .................. 195/103.5 M; 195/100; 195/102
[51] Int. Cl.² .................. C12K 1/04; C12K 1/10; G01N 33/16
[58] Field of Search ............ 195/99, 100, 101, 102, 195/103.5 R, 103.5 M

[56] References Cited

UNITED STATES PATENTS

| | | | |
|---|---|---|---|
| 3,496,066 | 2/1970 | Berger et al. | 195/100 X |
| 3,928,141 | 12/1975 | Sosnowski | 195/103.5 R |

*Primary Examiner*—David M. Naff
*Assistant Examiner*—C. A. Fan
*Attorney, Agent, or Firm*—McDougall, Hersh & Scott

[57] ABSTRACT

A method for indicating the presence of microorganisms in blood or other fluids comprising introducing the material to be tested into a nutrient medium containing a ditetrazolium chloride which converts to detectable blue color component in response to dehydrogenase reduction which takes place when microorganisms are present, incubating the said nutrient medium for a short period of time, and then examining the incubated product whereby a blue coloration is indicative of the presence of microorganisms in the sample.

16 Claims, No Drawings

TEST PROCEDURE FOR MICROORGANISMS IN BLOOD

This invention relates to a colorometric method and composition for indicating the presence of microorganisms in whole blood.

To the present, such determinations are made by incubating a bottle of whole blood at 37° C. Segments are cultured out after 2 days and frequently thereafter for a period of 2 weeks, to determine whether microorganisms are present in the blood. The isolated cultures are tested with various antibiotics to determine the presence of microorganism antibiotic sensitivity.

The procedure for determination of the presence of microorganisms in the blood is subject to a number of objections. A principal objection is the time required to make such determination. The 2 week period is prescribed because some microorganisms are slow growing and detection might be missed with cultures made over a shorter period of time. Further objections reside in the risk of contamination, as a result of using a contaminated bottle or introducing a contaminant during the removal of a number of aliquots required to be taken periodically from the blood bottle, with the result that reliability of the test is minimized.

It is an object of this invention to provide a new and improved composition and method for colorometric determination of microorganism in whole blood, in which the determination can be made under aseptic conditions thereby to avoid contamination with corresponding greater reliability in the results obtained; in which the composition and method can be used in clinical microbiology for determination for the presence of the substantially entire range of microorganisms including aerobic, facultative and anaerobic types, down to the extremely oxygen sensitive (EOS) microorganisms which have heretofore presented problems requiring special techniques for detection; in which the test procedure can be carried out in a simple and efficient manner for substantially quicker determination of the presence of microorganism in the blood, without the prolonged time lapse required for culturing the blood or the removal of multiple aliquots over a long period of time; and in which visual determination can be made of the results.

In order to make a method of the type described available, it is important to make use of a colorometric constituent that is stable and non-reactive with constituents in blood; has good shelf life to enable storage of the test package over an extended period of time; the good color stability, while being substantially colorless, especially in the amount employed in the nutrient medium so as not to interfere with the detection of color change in response to the presence of microorganisms in the blood, and in which microbial contamination can be detected before use of the nutrient medium for test purposes.

It has been found that the above objective and requirement can be achieved, in a colorometric determination of this invention, when use is made of a nutrient medium containing a tetrazolium salt which is relatively colorless, but which is converted to a color, preferably a blue color, in response to dehydrogenase (reduction) formed in the nutrient medium in the presence of microorganisms in the blood.

Representative of the tetrazolium salts that may be used as an ingredient in the nutrient medium are the ditetrazolium salts having the general formula

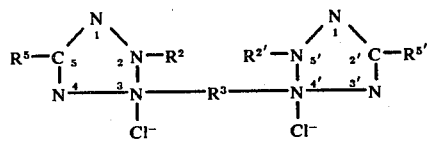

in which $R^2$ and $R^{2'}$, $R^5$ and $R^{5'}$ may be phenyl, p-nitrophenyl, m-nitrophenyl, anisyl, piperonyl-3, 3,4-dimethoxyphenyl and the like aromatic compounds, with or without substitution at the meta and/or para position with $C_1$ to $C_5$ alkoxy, nitro, or halogen groups; and $R^3$ is biphenylene, $C_1$ to $C_5$ alkoxy biphenylene such as 3-3'-dimethoxybiphenylene.

As the tetrazolium compound it is preferred to make use of 2,2',5,5'-tetraphenyl-3(3,3'-dimethoxy-4,4'phenylene) purple-ditetrazolium chloride, referred to in the trade as Blue Tetrazolium. Other ditetrazolium chlorides can be used such as 2,2',5,5'-tetraphenyl-3,3'(p-biphenylene) ditetrazolium chloride 2,2'-diphenyl-3,-(4,4'-biphenylene)-5,5'-di-m-nitrophenyl ditetrazolium chloride and preferably
2,2'-di-p-nitrophenyl-3,-(3,3'-dimethoxy-4,4'-biphenylene) 5,5'-di-p-anisyl-ditetrazolium chloride
2,2'-diphenyl-5,5'-di-p-anisyl-3,-(3,3'-dimethoxy 4,4'biphenylene-di-tetrazolium chloride
2,2'-di-p-nitrophenyl-3,-(3,3'-dimethoxy-4,4'-biphenylene)- 5,5' diphenyl-ditetrazolium chloride
2,2'-diphenyl-3,(3,3'-dimethoxy-4,4'-diphenylene)- 5,5'-di-m-nitrophenyl-ditetrazolium chloride
2,2'-diphenyl-5,5'-dipiperonyl-3-(3,3'-dimethoxy-4,4'-biphenylene-ditetrazolium chloride
2,2'-diphenyl-3,(3,3'-dimethoxy-4,4'-diphenylene-5,5'-di- (3,4-dimethoxyphenyl) ditetrazolium chloride.

Characteristic of the above ditetrazolium compounds, which are uniquely employed in the practice of this invention, is the blue dye color component that is released upon the severence of the N—N groups in response to hydrogenase reduction when microorganisms are present in the blood. This blue dye component is easily recognizable, either visually or by instrumentation, even in the presence of the color components in whole blood.

The tetrazolium salt should not be employed in the nutrient medium in an amount that might interfere with microbiological growth. At the same time, it should be present in the concentration capable of development of a detectable blue color in the medium.

The desired results can be secured when the ditetrazolium chloride or other tetrazolium salt is present in the nutrient medium in an amount of at least 0.0002 grams per 100 cc of medium and preferably in an amount within the range of 0.0005 to 0.02 grams per 100 cc of medium. It is desirable to make use of a level of the blue ditetrazolium chloride which is as low as possible, in order to minimize any inhibitory effects.

In practice, it is desirable to form a shock solution of the tetrazolium salt, as by dissolving the salt first in a small amount of alcohol, such as ethanol. The solution is diluted with a relatively large proportion of distilled water and then autoclaved for aseptic addition in the desired increments to the nutrient medium to give the desired concentration.

The following is representative of a preferred nutrient medium for use in the practice of this invention.

EXAMPLE 1

Culture medium:

| Amount | Ingredient |
|---|---|
| 7.5 grams per liter | Tryptic Soy broth (Difco) |
| 2.5 grams per liter | Glucose |
| 13.5 grams per liter | Sodium succinate |
| 5.6 grams per liter | Sodium lactate |
| 25.0 cc | Blue tetrazolium (0.05% solution) |
| 975.0 cc | Buffer solution of Example 1(A) (pH 7.4) |

EXAMPLE 1(A)

Buffer solution (pH 7.4):

| Amount | Ingredient |
|---|---|
| 1 gram mol | Tris(hydroxymethyl)amino-methane |
| 0.1 gram mol | $MgSO_4$ |
| 0.2 gram mol | $CaCl_2$ |
| 0.6 gram mol | KCl |
| 7.0 gram mols | NaCl |
| 1000 cc | Distilled water |

The blue tetrazolium is first dissolved in ethyl alcohol in the amount of 0.025 grams of blue tetrazolium in 2 cc ethyl alcohol, and the solution is diluted with 48 cc of distilled water. The solution is autoclaved and the 25 cc increment is added, as in Example 1, to yield a nutrient containing 0.0003 grams of blue tetrazolium per 50 cc of the above indicated nutrient medium. Addition can be made of the solution of blue tetrazolium at any time prior to use of the nutrient medium in the blood test.

EXAMPLE 2

Culture Medium:

| Amount | Ingredient |
|---|---|
| 17 grams per liter | MR-VP Medium (Difco) (methyl red-voges prospauer containing (a) buffer peptone 7 g/l, (b) bacto-dextrose 5 g/l and (c) dipotassium phosphate 5 g/l) |
| 5 grams per liter | Meat peptone (Gibco peptone 105) |
| 4 grams per liter | Yeast extract (Difco) |
| 5 grams per liter | NaCl |
| 10 grams per liter | Gelatin |
| 0.2 gram per liter | Magnesium sulfate ($MgSO_4$, anhydrous) |
| 5.6 grams per liter | Sodium lactate |
| 13.5 grams per liter | Sodium succinate |
| 0.5 gram per liter | Calcium chloride |
| 0.1 gram per liter | Glutamic Acid |
| 0.3 gram per liter | Sodium polyanetholesulfonate |
| 0.03 gram per liter | l-Cysteine hydrochloride |
| 3.0 grams per liter | Starch |
| 6.05 grams per liter | Tris buffer [Tris(hydroxymethyl)amino-methane] |
| 0.34 gram per liter | EDTA (sodium salt) |
| 2.0 grams per liter | Sodium Bicarbonate |
| 8 cc. of a 0.1% solution | Blue tetrazolium |

It is desirable to prepare the nutrient medium of Examples 1 or 2 well in advance of use in order to detect microbiological contamination. This is indicated by the development of a blue color prior to use. Thus, any contaminated bottles can be discarded prior to use thereby to make the test more effective and more reliable.

The succinate and lactate are effective substrates in the nutrient medium to trigger the enzymatic reduction by stimulating the activity of succinate dehydrogenase and/or lactic dehydrogenase. Such succinate and/or lactate can be embodied in the nutrient medium as a soluble salt, such as an alkali metal salt, as represented by sodium or potassium succinate, sodium or potassium lactate. Use in corresponding amounts can also be made of the corresponding sodium isocitrate or potassium isocitrate. The amount of soluble succinate, lactate or isocitrate is critical. Instead of succinate, lactate or isocitrate, other metabolides can be employed as an ingredient in the nutrient medium to accelerate the reduction reaction. Such metabolites can be present in an amount up to about 5% by weight of the nutrient medium but insufficient to induce chemical reaction to the ditetrazolium chloride prior to exposing the composition to a blood sample.

Glucose or other carbohydrates are added to provide nutrient for growth and furnish an additional source of hydrogen in the event that the amount of reducing compound is insufficient in the nutrient medium, or in order to insure sufficiency. It is undesirable to make use of an excessive amount of reducing agent, otherwise reduction may be in response to a chemical reduction reaction instead of the desired microbiological reaction based upon the presence of microorganisms in the blood.

Since the rate of growth of the organism is controlled somewhat by the pH of the medium, it is desirable to adjust for a pH for optimum bacterial growth. For this purpose, it is desirable to provide for a LC within the range of 6.8 to 7.8 and preferably a pH which is near to normal blood pH, or a pH of about 7.2. This is accomplished by means of the Tris-buffer illustrated in Examples 1 and 2. Other buffers or buffer compositions can be employed to maintain the desired pH of the nutrient medium in the blood test.

The buffer component can be separately formulated as a solution added to the nutrient medium in an amount to give the desired titer, or the ingredients can be added directly during formulation of the nutrient medium.

Since the ions of sodium and potassium tend to enhance or catalyze microbiological growth, it is desirable to incorporate various of the salts, such as the succinates, or lactates of the nutrient medium, or the salts in the buffer as their corresponding sodium or potassium salts.

As illustrated in Example 1, it is desirable to sterilize the nutrient medium separate and apart from the blue tetrazolium or other ditetrazolium chloride and then add the blue tetrazolium to the sterilized nutrient medium. Any development of a blue color prior to use in the whole blood test would thus be indicative of contamination of the nutrient medium with microorganisms. Any such contaminated bottles could then be eliminated before use. As a result, the blood test could be limited to bottles in which there was no microorganism contamination thus enhancing the reliability of the test.

In carrying out the test for the presence of microorganisms in whole blood, 5 cc of blood is introduced aseptically into a blood bottle containing 50 cc of the nutrient medium. The bottle is then incubated at 37° C for a period of time which may range from several hours to a few days and preferably over night. The incubated bottle is then examined. The presence of a blue color is indicative of the presence of microorganisms in the blood. The absence of a blue coloration indicates that the blood is free of viable growing microorganisms.

It will be apparent that the test is a qualitative test to determine the presence or absence of microorganisms as distinguished from the amount and type of microorganisms. The test can also be used to determine the presence or absence of microorganisms in substances other than blood.

Since the presence of microorganism in the blood is indicated, in accordance with the practice of this invention, by a change from colorless to blue, the test procedure is effective to detect any amount of organism in the blood whereas color change from one color to another would be difficult to detect without intense color generation. For example, generation of a red, yellow, orange and the like color in response to the presence of microorganism in the blood would be impractical because of the proximity to the color of red blood.

It will be apparent from the foregoing that we have provided a simple and effective test for microorganism in whole blood, which test is reliable and can be carried out quickly and efficiently.

It will be understood that changes may be made in the details of formulation and operation without departing from the spirit of the invention, especially as defined in the following claims.

We claim:

1. A method for indicating the presence of microorganisms in blood samples comprising introducing the blood into a nutrient medium having a pH within the range of 6.8 to 7.5 containing a ditetrazolium chloride which converts to a detectable blue color component in response to microbial dehydrogenase reduction which takes place when microorganisms are present in the blood, incubating the nutrient medium contained in the sample for a short period of time and then examining the incubated product to detect the presence of microorganisms as indicated by a blue color formed by reduction of the ditetrazolium chloride in which the ditetrazolium chloride has the general formula

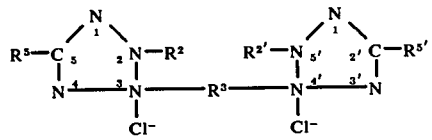

in which $R^2, R^{2'}, R^5, R^{5'}$ are aromatic groups which may be substituted on the meta or para position with groups selected from the group selected from $C_1$ to $C_5$ alkoxy, nitro and halogen groups, $R^3$ is biphenylene or $C_1$ to $C_5$ alkoxy biphenylene.

2. A ditetrazolium chloride as claimed in claim 1 in which $R^2, R^{2'}, R^5, R^{5'}$ are groups selected from the group consisting of phenyl, p-nitrophenyl, m-nitrophenyl, anisyl, piperonyl-3, and 3,4-dimethoxyphenyl.

3. A method as claimed in claim 1 in which the ditetrazolium chloride is 2,2',5,5'-tetraphenyl-3(3,3'-dimethoxy-4,4'-biphenylene) purple-ditetrazolium chloride.

4. A method as claimed in claim 1 in which the ditetrazolium chloride is present in the nutrient medium in an amount of at least 0.0002 gram per 100 cc.

5. A method as claimed in claim 1 in which the ditetrazolium chloride is present in the nutrient medium in an amount within the range of 0.0005 to 0.02 gram per 100 cc.

6. A method as claimed in claim 1 in which the nutrient medium is sterilized prior to the addition of the ditetrazolium chloride.

7. A method as claimed in claim 1 in which the ditetrazolium chloride is added to the nutrient medium in the form of a solution which has been sterilized before addition to the nutrient medium.

8. A method as claimed in claim 1 in which the nutrient medium contains substrates which facilitate the enzymatic reduction of the ditetrazolium chloride.

9. A method as claimed in claim 8 in which the substrate is selected from the group consisting of a soluble succinate, lactate and isocitrate.

10. A method as claimed in claim 9 in which the substrate is present in an amount up to 1.2% by weight of the nutrient medium.

11. A method as claimed in claim 9 in which the substrate is present in an amount within the range of 0.1 to 1.2% by weight.

12. A method as claimed in claim 1 in which the nutrient medium is at a pH of about 7.2.

13. A method as claimed in claim 1 in which addition is made to the nutrient medium of a buffer composition to maintain the desired pH level.

14. A method as claimed in claim 1 in which the nutrient medium contains a carbohydrate as a source for additional hydrogen.

15. A method as claimed in claim 14 in which the carbohydrate is glucose.

16. A blood microorganism-detecting composition comprising a nutrient medium having a pH within the range of about 6.8 to 7.5 and capable of supporting the growth of microorganisms under incubating conditions, and which contains as an essential ingredient, a ditetrazolium chloride having the general formula of claim 1 which is characterized by the generation of a blue color when exposed to the dehydrogenase elaborated by growing microorganisms and is present in an amount within the range of 0.0002 – 0.02 grams per 100 cc of medium, a substrate selected from the group consisting of a soluble succinate, lactate and isocitrate in an amount sufficient to trigger enzymatic reduction without chemical reduction of the ditetrazolium chloride in the absence of microorganism, and a buffer present in an amount to maintain the pH within the range of 6.8 to 7.5.

* * * * *

UNITED STATES PATENT OFFICE
CERTIFICATE OF CORRECTION

Patent No. 4,026,767    Dated May 31, 1977

Inventor(s) Chun-Nan Shih and Edward Balish

It is certified that error appears in the above-identified patent and that said Letters Patent are hereby corrected as shown below:

column 4, line 34, change "L.C." to -- pH --

Signed and Sealed this

Twentieth Day of September 197

[SEAL]

Attest:

RUTH C. MASON
*Attesting Officer*

LUTRELLE F. PARKER
*Acting Commissioner of Patents and Trademark*